(12) United States Patent
McKinnon

(10) Patent No.: US 8,974,411 B2
(45) Date of Patent: Mar. 10, 2015

(54) CONICAL DIFFUSER TIP

(75) Inventor: Austin Jason McKinnon, Herriman, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 164 days.

(21) Appl. No.: 12/124,757

(22) Filed: May 21, 2008

(65) Prior Publication Data

US 2009/0292272 A1 Nov. 26, 2009

(51) Int. Cl.
| A61M 1/00 | (2006.01) |
|---|---|
| A61M 31/00 | (2006.01) |
| A61M 25/00 | (2006.01) |
| A61M 5/00 | (2006.01) |
| A61M 25/06 | (2006.01) |

(52) U.S. Cl.
CPC ....... *A61M 25/0068* (2013.01); *A61M 25/0668* (2013.01); *A61M 25/065* (2013.01); *A61M 25/0069* (2013.01); *A61M 2025/0073* (2013.01)
USPC ......... 604/118; 604/93.01; 604/264; 604/246

(58) Field of Classification Search
CPC ...................... A61M 25/0068; A61M 25/0067; A61M 25/00; A61M 2025/0073; A61M 25/0069
USPC .................. 604/523, 277–279, 68–70, 93.01, 604/96.01, 246, 118, 30
See application file for complete search history.

(56) References Cited

U.S. PATENT DOCUMENTS

| 3,386,438 | A | | 6/1968 | Stevens | |
|---|---|---|---|---|---|
| 3,713,442 | A | * | 1/1973 | Walter | 604/161 |
| 4,563,180 | A | * | 1/1986 | Jervis et al. | 604/523 |
| 4,961,731 | A | | 10/1990 | Bodicky et al. | |
| 5,085,635 | A | | 2/1992 | Cragg | |
| 5,578,006 | A | * | 11/1996 | Schon | 604/93.01 |
| 5,616,137 | A | | 4/1997 | Lindsay | |
| 5,843,017 | A | * | 12/1998 | Yoon | 604/22 |
| 5,857,464 | A | | 1/1999 | Desai | |
| 6,052,612 | A | | 4/2000 | Desai | |
| 6,132,405 | A | * | 10/2000 | Nilsson et al. | 604/264 |
| 6,293,958 | B1 | | 9/2001 | Berry et al. | |
| 6,547,769 | B2 | | 4/2003 | VanTassel et al. | |
| 6,641,564 | B1 | | 11/2003 | Kraus | |
| 6,669,679 | B1 | * | 12/2003 | Savage et al. | 604/500 |
| 6,866,655 | B2 | | 3/2005 | Hackett | |
| 2002/0072712 | A1 | | 6/2002 | Nool et al. | |
| 2003/0023200 | A1 | | 1/2003 | Barbut et al. | |
| 2004/0116901 | A1 | * | 6/2004 | Appling | 604/523 |
| 2005/0038411 | A1 | * | 2/2005 | Okada | 604/523 |

(Continued)

FOREIGN PATENT DOCUMENTS

| JP | 3018993 U | 12/1995 |
|---|---|---|
| JP | H08322940 A | 12/1996 |
| JP | 2001-340469 | 12/2001 |

*Primary Examiner* — Kevin C Sirmons
*Assistant Examiner* — Bradley G Thomas, Jr.
(74) *Attorney, Agent, or Firm* — Jeanne Lukasavage; Craig Metcalf; Kirton McConkie

(57) ABSTRACT

A catheter assembly is provided having a conical diffuser tip for use in rapid infusion procedures. The conical diffuser tip provides a flared opening whereby the velocity of an infusant is decreased as the infusant travels through the catheter tip and exits into the vascular system of a patient. This decrease in velocity proportionately reduces the backpressure and/or recoil force of the catheter assembly thereby permitting the use of higher infusion rates. The catheter tip is introduced into the vasculature of a patient via a splittable introducer needle.

20 Claims, 8 Drawing Sheets

(56) References Cited

U.S. PATENT DOCUMENTS

2005/0124969 A1* 6/2005 Fitzgerald et al. ............ 604/508
2006/0184048 A1* 8/2006 Saadat .......................... 600/478
2007/0073271 A1 3/2007 Brucker et al.

* cited by examiner

CONICAL DIFFUSER TIP

BACKGROUND OF THE INVENTION

The present disclosure relates generally to vascular access devices and methods, including catheter assemblies and devices used with catheter assemblies. Generally, vascular access devices are used for communicating fluid with the vascular system of patients. For example, catheters are used for infusing fluid, such as saline solution, various medicaments, and/or total parenteral nutrition, into a patient, withdrawing blood from a patient, and/or monitoring various parameters of the patient's vascular system.

A variety of clinical circumstances, including massive trauma, major surgical procedures, massive burns, and certain disease states, such as pancreatitis and diabetic ketoacidosis, can produce profound circulatory volume depletion. This depletion can be caused either from actual blood loss or from internal fluid imbalance. In these clinical settings, it is frequently necessary to infuse blood and/or other fluid rapidly into a patient to avert serious consequences.

Additionally, the ability to inject large quantities of fluid in a rapid manner may be desirable for certain other medical and diagnostic procedures. For example, a power injection of a contrast agent may be desirable for conducting a scanning procedure, such as a computed tomography (CT) scan. For this procedure, an injection rate of about 1 to 10 ml/second is needed to ensure sufficient distribution of the contrast agent during the scanning procedure. A power injection of a highly viscous liquid may also be desirable. For example, a medical or diagnostic procedure may require a rapid injection of a fluid with a high viscosity at an injection rate of about 1 to 10 ml/second. Power injections at this injection rate produce significant back pressure within the infusion system that may result in a failure of the infusion system components.

In the past, power injection of highly viscous fluids, as well as rapid infusions to replace large amounts of fluids has been a major problem to the medical and surgical teams attending patients with these acute needs. A common method of rapid infusion involves the simultaneous use of a plurality of infusion sites. Frequently, a plurality of medical personnel is required to establish and oversee the various infusion sites and to ensure the flow of fluids from their respective fluid sources. This method may be limited by the number of peripheral or central sites that can be physically accessed in a given patient, the number of people attending the fluids being infused, as well as the efficiency of infusing the fluids during a dire, hypovolemic event. It is not uncommon for four to five anesthesiologists or technicians to stand in attendance during transplant operations lasting more than twenty-four hours attempting to infuse massive quantities of blood through five or six venous catheters.

Patients who have undergone massive trauma or surgery such as liver transplantations or other elective procedures may require voluminous quantities of fluids to maintain a viable circulatory state. Although it is not uncommon for an anesthesiologist or surgeon in a major trauma center to encounter massive exsanguinations of ten liters or more, it is unusual to successfully resuscitate a patient with such massive blood volume loss using traditional methods.

Traditionally, rapid infusion therapy entails the use of a venous catheter attached to a peristaltic pump and a fluid source. A patient is infused as a tip portion of the catheter is inserted into the vasculature of a patient and the pump forces a fluid through the catheter and into the patient's vein. Intravenous infusion rates may be defined as either routine, generally up to 999 cubic centimeters per hour (cc/hr), or rapid, generally between about 999 cc/hr and 90,000 cc/hr (1.5 liters per minute) or higher. Current rapid infusion therapies utilize a catheter and catheter tip with geometries identical to those used with traditional, routine infusion rates. These geometries include a tapering catheter tip such that the velocity of a fluid is accelerated as the fluid moves through the catheter tip and exits into a patient's vasculature. This acceleration of the infused fluid is undesirable for several reasons.

For example, the tapered catheter results in a greater backpressure and/or recoil force for the remainder of the catheter assembly. This effect is undesirable due to the limitations of the pumping capacity of the infusion pump as well as the limited structural integrity of the components and subcomponents of the infusion system. For example, if the backpressure becomes too great, the pump's efficiency may decrease and certain seals or connections within the infusion system may fail. Additionally, a greater recoil force may cause the catheter tip to shift within the patient's vein thereby displacing the catheter and/or damaging the patient's vein and/or injection site.

Additionally, the accelerated infusant may infiltrate the patient's vein wall thereby damaging the patients vein and leading to extravasation. Not only is this uncomfortable and/or painful to the patient, but infiltration may also decrease the infusion rate and prevent the patient from receiving the needed infusant. Accordingly, the problem of backpressures and/or recoil forces during rapid infusion procedures remains to be solved. The present disclosure presents systems and methods to significantly limit and/or prevent such undesirable recoil forces during rapid infusion procedures.

BRIEF SUMMARY OF THE INVENTION

The systems and methods of the present disclosure have been developed in response to problems and needs in the art that have not yet been fully resolved by currently available infusion systems and methods. Thus, these systems and methods are developed to provide for safer and more efficient infusion procedures.

One aspect of the present disclosure provides a catheter for use in high pressure infusion therapies. The catheter includes a catheter tip, a catheter adapter and a length of catheter tubing. The catheter tubing is generally comprises a uniform bore. The bore of the catheter tubing is selected based on the needs of the infusion therapy. The catheter tip comprises a proximal end and a distal end.

The catheter tip is generally conical with the proximal end having an inner and outer diameter equal to the inner and outer diameter of the catheter tubing. The second end of the catheter tip comprises an inner and outer diameter that is larger than the inner and outer diameter of the first end of the catheter tip, respectively. Thus, the inner surface of the catheter tip splays outwardly from the first end to the second end in a conical manner. The resulting catheter tip is conically shaped and serves a diffusing function for an infusant with the catheter tip.

The geometry of the conical catheter tip reduces the recoil force of the catheter thereby allowing the use of higher flow rates for infusion therapies. Unlike the prior art catheters, the velocity of an infusant within the conically shaped catheter tip actually decreases from the first end to the second end of the catheter tip. By diffusing the infusant, the exit velocity of the infusant is reduced, thereby reducing the likelihood of venous infiltration. Additionally, the decreased exit velocity decreases the recoil force of the catheter. This reduces the likelihood of displacing the catheter during high pressure infusion therapies.

Several geometric factors must be considered when implementing the current invention. For example, a divergence angle for the catheter tip, as well as an area ratio and length must be selected for a targeted vasculature, infusant and infusion therapy. Each of these geometric factors is constrained by the targeted vasculature. For example, the divergence angle and length of the catheter tip must provide a maximum outlet diameter of the catheter tip that is approximately less than, or equal to 50% of inner diameter of the targeted vasculature. Therefore, in one embodiment the divergence angle is within a range of about 5-20° and the area ratio is within a range of about 2-30%.

The tip described above may also be incorporated into an infusion system. The infusion system may include a variety of components and subcomponents for a given infusion therapy. For example, an infusion system may include an infusion pump, a filtering device, access ports, an intravenous fluid source and/or an introducer needle.

Unlike conventional over-the-needle catheter systems, the flared, conical configuration requires the use of a splittable introducer needle. The catheter tip is compressed within a shaft of the splittable introducer needle such that the outer diameter of the compressed catheter tip is equal to, or less than the inner diameter of the needle shaft. As such, the catheter tubing and compressed catheter tip may be slidably housed within the needle shaft of the splittable introducer needle.

The splittable introducer needle is used to introduce the catheter into a vascular system of a patient. Following insertion of the needle, the catheter tip and catheter tubing are advanced into the patient's vein. The splittable introducer needle is then withdrawn from the patient and divided into at least two halves without disrupting the placement of the catheter tip. The catheter adapter may then be secured to the patient by any suitable technique.

Following advancement of the catheter tip into the vascular system of the patient, the compressed catheter tip relaxes and/or decompresses into the conical diffuser shape. Additionally or alternatively, the catheter tip may include a shrunken, dehydrated polymer material that is rehydrated and restored to the conical diffuser shape upon introduction into the aqueous environment of the patient's vascular system.

BRIEF DESCRIPTION OF THE SEVERAL
VIEWS OF THE DRAWINGS

In order that the manner in which the above-recited and other features and advantages of the invention are obtained will be readily understood, a more particular description of the invention briefly described above will be rendered by reference to specific embodiments thereof which are illustrated in the appended drawings. These drawings depict only typical embodiments of the invention and are not therefore to be considered to limit the scope of the invention.

DETAILED DESCRIPTION OF THE INVENTION

The presently preferred embodiments of the present invention will be best understood by reference to the drawings, wherein like reference numbers indicate identical or functionally similar elements. It will be readily understood that the components of the present invention, as generally described and illustrated in the figures herein, could be arranged and designed in a wide variety of different configurations. Thus, the following more detailed description, as represented in the figures, is not intended to limit the scope of the invention as claimed, but is merely representative of presently preferred embodiments of the invention.

Figure 1:
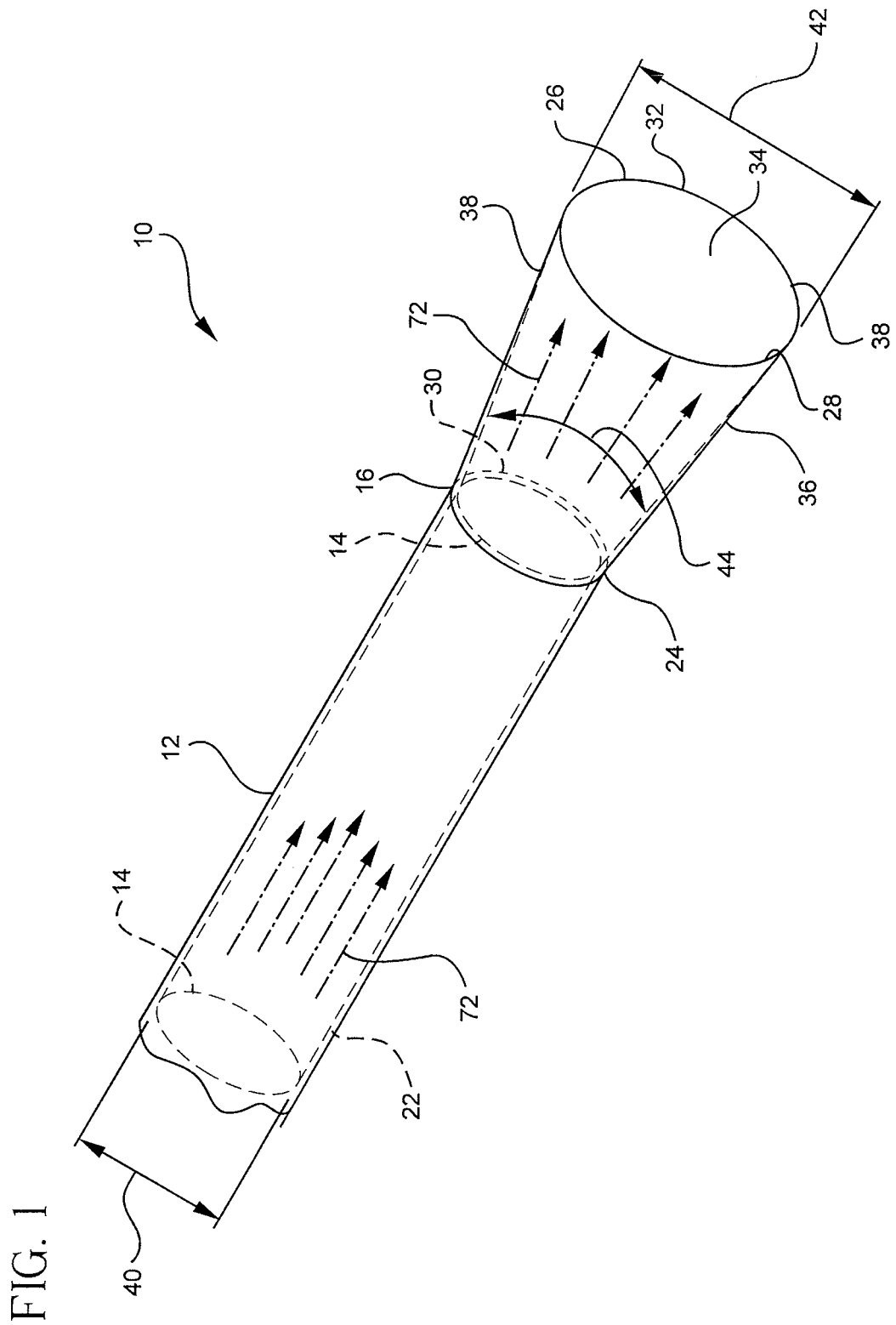
FIG. 1 is a perspective view of a catheter with a conical diffuser tip.

Referring now to FIG. 1, a section of a catheter 10 is illustrated. The catheter 10 comprises a catheter tube 12 and a catheter tip 18. The catheter tube 12 may comprise any length where the length is selected based on the intended application of the catheter 10. For example, the catheter 10 length may vary from a few centimeters for peripheral access to many centimeters for central access procedures.

The catheter tube 12 is generally tubular having an inner diameter 14. The tube wall 22 of the catheter tube 12 is generally uniform in thickness thereby providing a uniform bore along the entire length of the catheter tube 12. The catheter tube 12 adjoins the catheter tip 18 at the terminal end 16 of the catheter tube 12. The catheter tube 12 and the catheter tip 18 are generally comprised of the same material, but may be comprised of different materials as discussed in detail below.

The tube wall 22 thickness of the catheter tube 12 is selected so as to achieve a desired flexibility or rigidity for the catheter 10. The bore of the catheter tube 12 is selected based on the intended application of the catheter 10. For example, where an application calls for administration of a thick or viscous liquid, a large bore catheter tube may be desirable due to flow and volume restrictions of smaller bore catheter tubes. Additionally, where an application calls for administration of large volumes of a liquid, a large bore catheter tube may be desirable due to the flow and volume restrictions of small bore catheter tubes.

The diffuser catheter tip 18 comprises a first end 24 and a second end 26. The first end 24 adjoins the terminal end 16 of the catheter tube 12, as illustrated. Additionally, the second end 26 comprises a first opening 28 of the catheter 10. The catheter tip 18 further comprises a first inner diameter 30 and a second inner diameter 32. The first inner diameter 30 is equal to the inner diameter 14 of the terminal end 16 of the catheter tube 12. The second inner diameter 32 of the catheter tip 18 is greater than the first inner diameter 30 of the catheter tip 18.

The catheter tip 18 is generally conical. As such, the inner surface 34 of the catheter tip 18 gradually flares outward from the first inner diameter 30 to the second inner diameter 32 thereby forming a conical diffuser tip 18. Additionally, the inner surface 34 of the tube wall 38 is tapered such that the thickness of the tube wall 38 decreases or thins from the first end 24 to the second end 26. Thus, the tube wall 38 thickness terminates at the first opening 28 of the catheter 10. Conversely, the outer surface 36 of the tube wall 38 is generally planer and comprises a generally conical shape as previously described.

Figure 2:
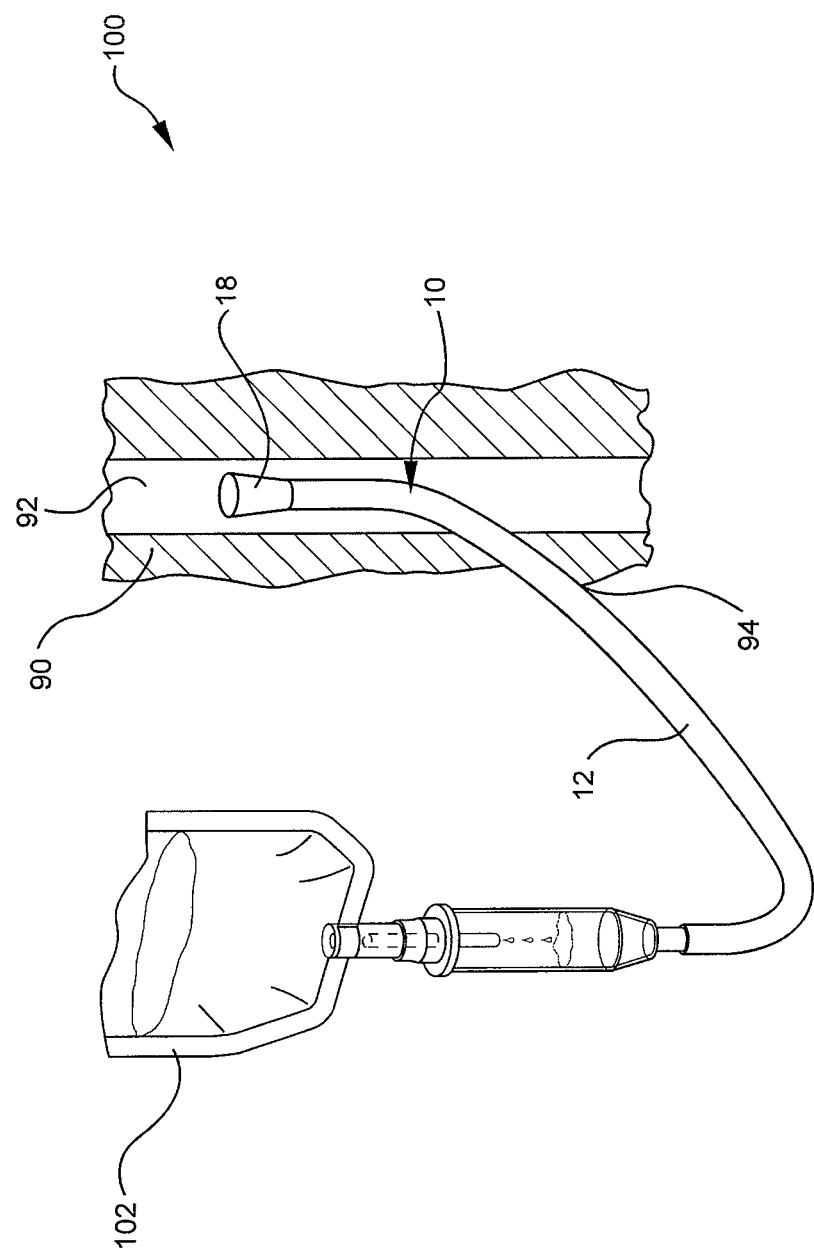
FIG. 2 is a perspective view of a catheter with a conical diffuser tip as incorporated into an infusion system.

Referring now to FIG. 2, the catheter 10 is illustrated as incorporated into an infusion system 100. The infusion system 100 may include a variety of components and/or subcomponents for various infusion therapies. For example, the infusion system 100 may include an infusion pump, such as a peristaltic pump, as well as a filtering device. The infusion system 100 may also include a power injector for injecting CT scan contrast agents, as well as fluids of high viscosity as required for various medical and diagnostic procedures. Additionally, the catheter tubing 12 may include a plurality of access ports for accessing the infusion system 100. The infusion system 100 may also include an introducer needle as well as an adapter to house the introducer needle. Configurations of connectors, splicers and/or adapters may also be incorporated into the infusion system 100 within the scope of the current invention.

As illustrated, the infusion system 100 includes a section of catheter tubing 12, a catheter 10 and an intravenous (IV) fluid source 102. The catheter tubing 12 is connected to the IV fluid source 102 and the catheter 10. A fluid from the IV fluid source 102 is infused into a patient 90 following insertion of the catheter tip 18 through an insertion site 94 and into the vascular system 92. As such, a fluid communication is established between the IV fluid source and the vascular system 92 of the patient 90.

Figure 3:
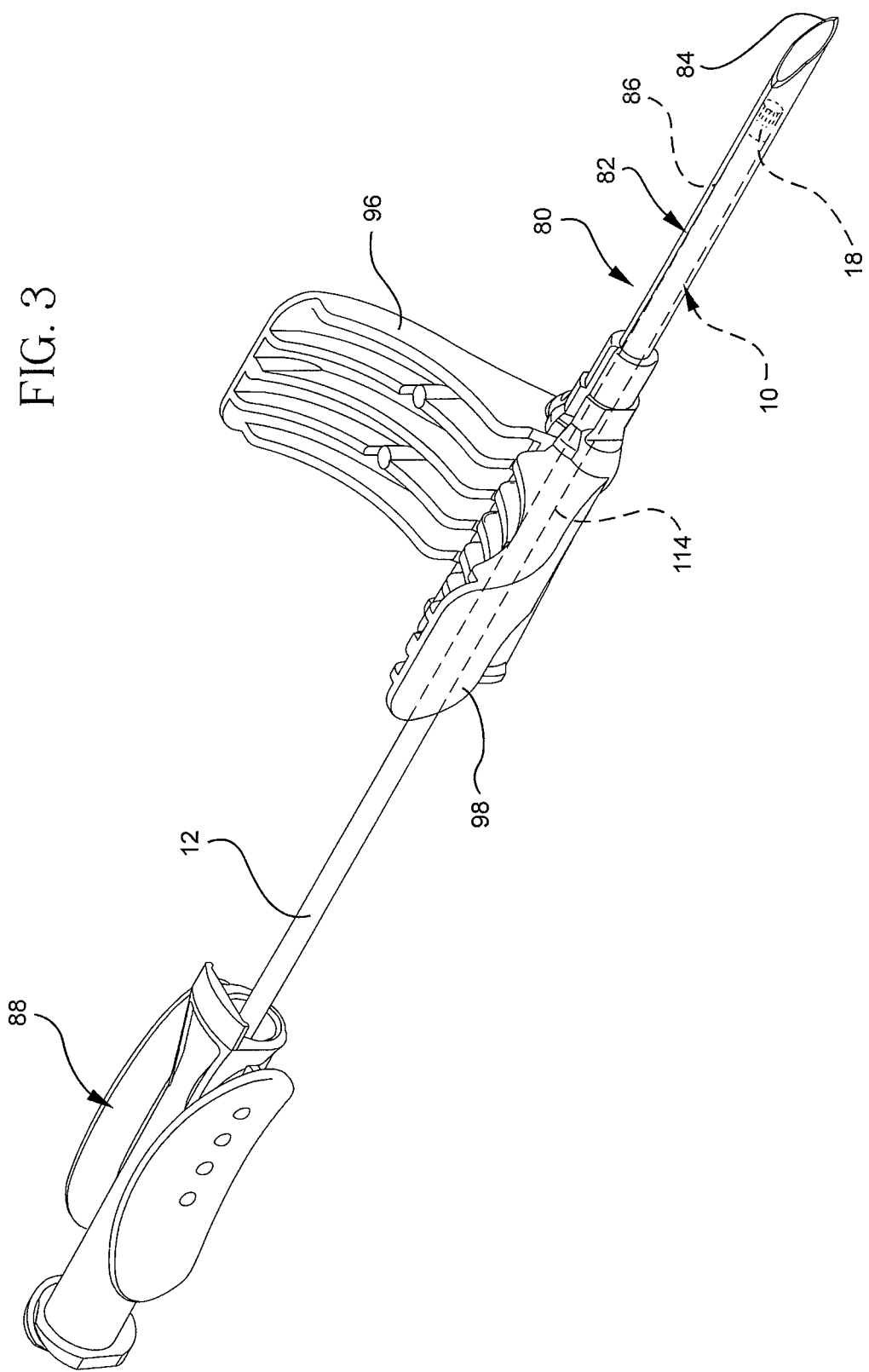
FIG. 3 is a perspective view of a catheter with a conical diffuser tip as housed within a splittable introducer needle.
Figure 3A:
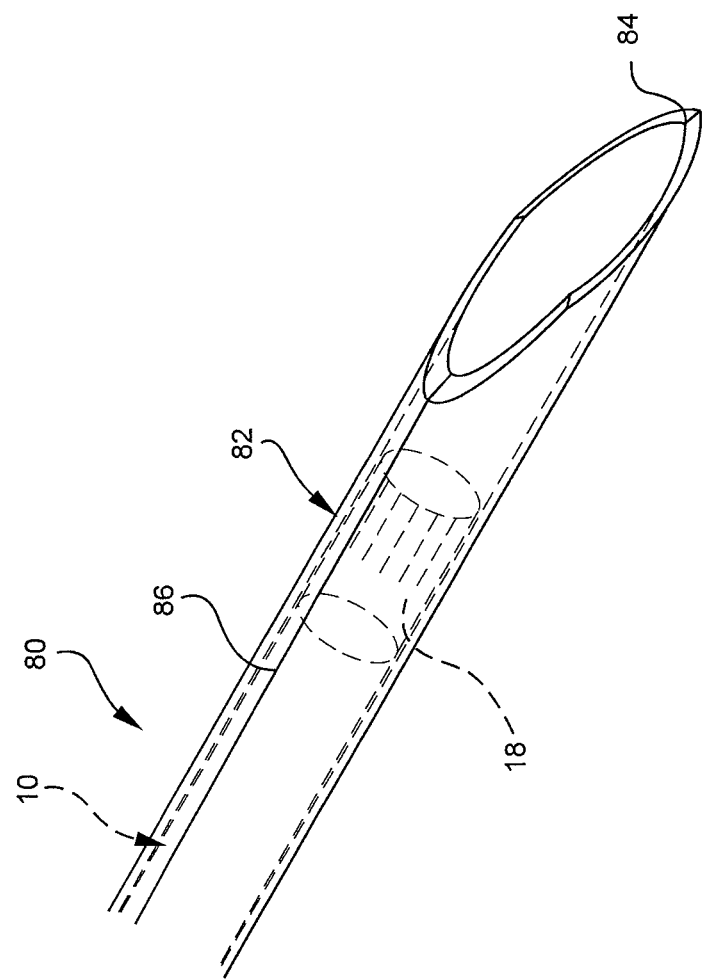
FIG. 3a is a detailed perspective view of a conical diffuser tip as compressed within the tip of a splittable introducer needle.
Figure 4:
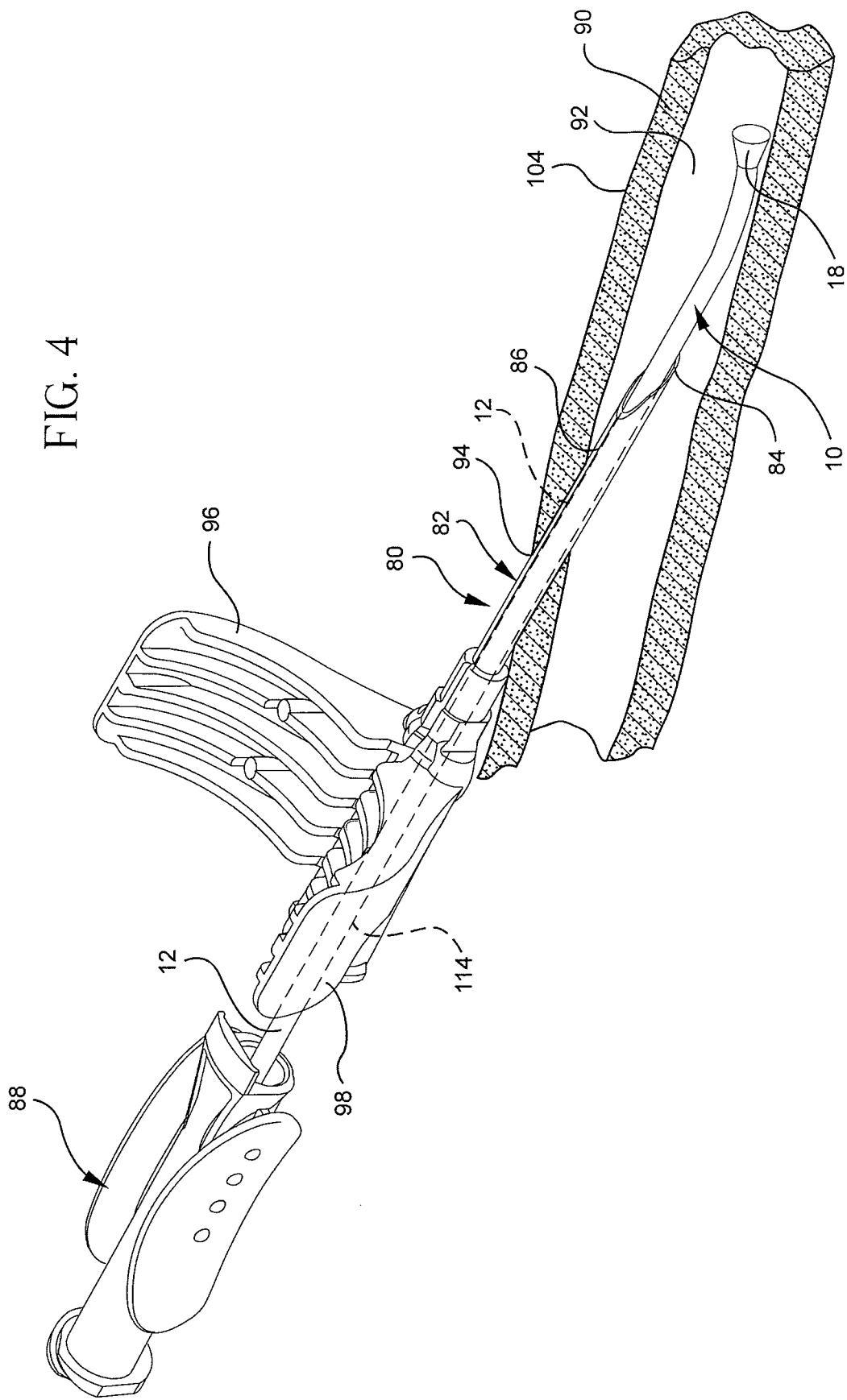
FIG. 4 is a perspective view of a catheter with a conical diffuser tip as inserted into a cross-sectioned patient via a splittable introducer needle.
Figure 5:
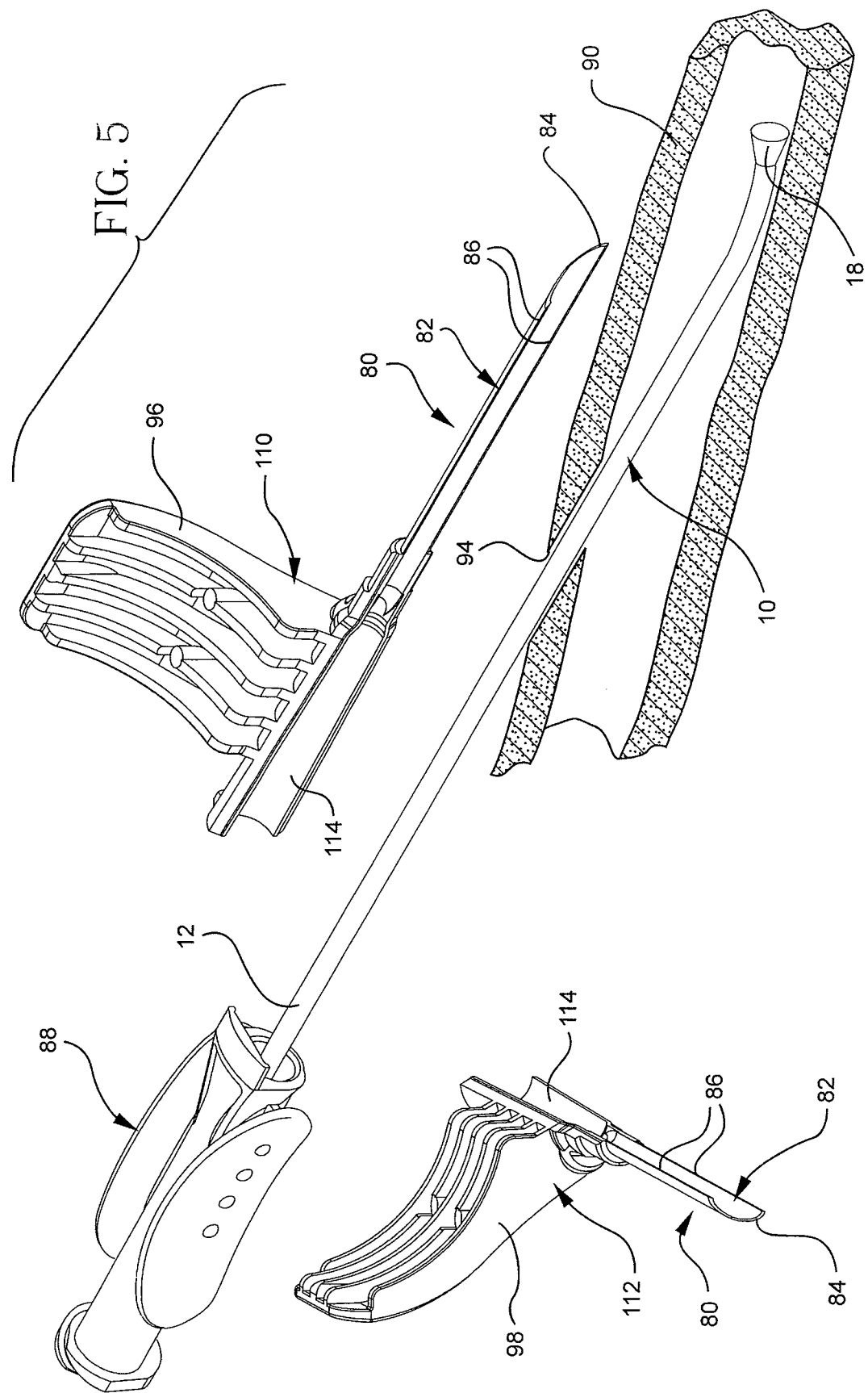
FIG. 5 is a perspective view of a catheter with a conical diffuser tip following a division of the splittable introducer needle.

Referring now to FIGS. 3-5, unlike conventional over-the-needle catheter systems, the current catheter 10 is introduced into the vascular system 92 of a patient 90 via a splittable introducer needle 80. The splittable introducer needle 80 comprises a needle shaft 82 and a needle tip 84. The needle tip 84 is beveled so as to provide a cutting surface for piercing a patient's skin 90. The needle shaft 82 comprises an inner diameter selected to slidably house the catheter 10, catheter tubing 12 and the catheter tip 18. The catheter tip 18 is compressed into a fluted configuration such that the outer diameter of the compressed catheter tip 18 is less than, or equal to the inner diameter of the splittable needle shaft 82 (see FIG. 3a for detail). As such, the catheter tip 18 is slidably housed within the needle shaft 82, as illustrated.

The needle shaft 82 further comprises at least two score marks 86. The score marks 86 are located opposite one another and comprise a groove running the length of the needle shaft 82. The score marks are located on the inner surface of the needle shaft 82 thereby providing a smooth outer surface for the needle shaft 82. The score marks 86 provide at least two thinned portions of the needle shaft 82 where the needle shaft 82 may be easily separated into at least two pieces.

The splittable introducer needle 80 further comprises a first and second gripping handles 96, 98. The gripping handles 96, 98 are attached to a distal half 110 and a proximal half 112 of the splittable introducer needle 80, respectively. The gripping handles 96, 98 may be used for holding and maneuvering the needle shaft 82 during insertion. Additionally, the first and second gripping handles 96, 98 provide a gripping surface for separating the splittable introducer needle 80 following insertion of the catheter 10. Finally, the splittable introducer needle 80 comprises a channel 114 through which the catheter tubing 12 may slidably extend.

Referring now to FIG. 4, the catheter 10 is illustrated during insertion into a patient 90 via a splittable introducer needle 80. As illustrated, the needle tip 84 is used to penetrate the patient 90 at an insertion site 94. Following penetration, the needle tip 84 is advanced into the vascular system 92 of the patient 90. A user then advances the catheter tip 18 beyond the needle tip 82 and into the vascular system 92. A user may advance the catheter tip 18 by pushing the catheter adapter 88 towards the first and second gripping handles 96, 98 of the splittable introducer needle 80. Once the catheter tip 18 is inserted into the vascular system 92, a user may occlude the vascular system at an external point 104 adjacent the catheter tip 18. By so doing, the user may immobilize the catheter tip 18 within the vascular system 92. After immobilizing the catheter tip 18, the user may remove the needle tip 84 and needle shaft 82 from the patient 90 while leaving the catheter tip 18 within the vascular system 92.

Following advancement of the catheter tip 18 into the vascular system 92, the compressed catheter tip 18 may relax and uncompress. The decompression of the catheter tip 18 may be accomplished by any means. For example, in one embodiment the catheter tip 18 is mechanically compressed due to the restricted inner diameter of the needle shaft 82. As such, when the compressed catheter tip 18 is no longer housed within the needle shaft 82, the catheter tip 18 is no longer mechanically compressed and may therefore relax and uncompress.

Conversely, in another embodiment the catheter tip 18 is constructed of a dehydrated material, such as a dehydrated polymer. As such, the compressed state of the catheter tip 18 is a result of the shrunken state of the dehydrated material. Thus, when the catheter tip 18 is exposed to the aqueous environment of the vascular system 92 the dehydrated material is hydrated and the catheter tip 18 expands. In this embodiment, the dehydrated catheter tip 18 may be fused to the hydrated catheter 10 by any method of plastic joining. For example, the plastic joining method may include induction, electrofusion, laser welding, mechanical bonding and/or chemical bonding.

Referring now to FIG. 5, the splittable introducer needle 80 is illustrated as divided into a first half 110 and a second half 112. The channel 114 of the needle shaft 82 is shown housing a portion of the catheter tubing 12. Additionally, the score marks 86 are illustrated running the length of each half 110, 112 of the needle shaft 82. The splittable introducer needle 80, as illustrated, is one form of a splittable introducer needle compatible with the present invention. However, it is anticipated that any splittable introducer needle may used and/or adapted for use with the conical diffuser tip 18. Additionally, other methods of inserting a catheter 10 comprising the conical diffuser tip 18 may be used, such as surgical implantation.

Figure 6:
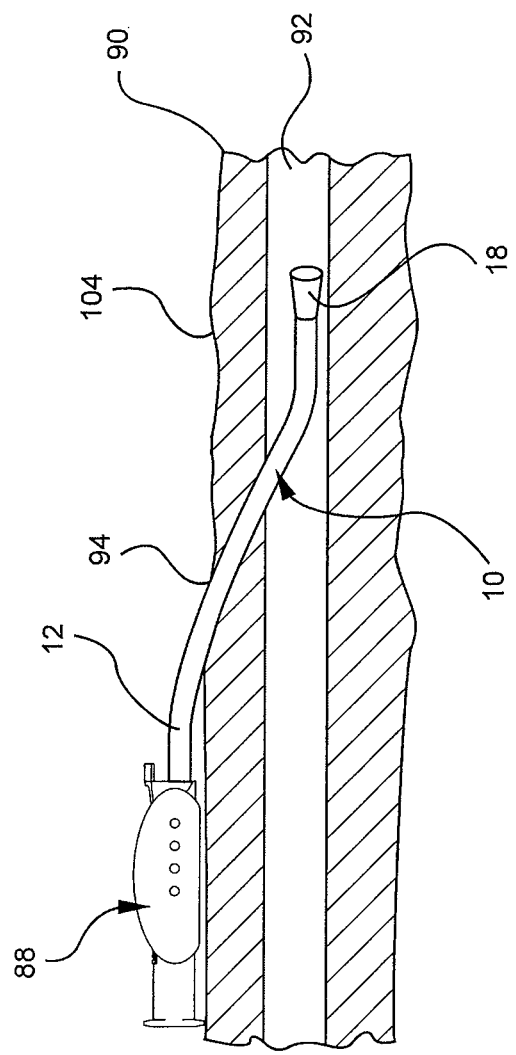
FIG. 6 is a perspective view of a catheter with a conical diffuser tip as inserted into a cross-sectioned patient, following removal of the splittable introducer needle.

Referring now to FIG. 6, a catheter 10 is illustrated following removal of the splittable introducer needle 80. The catheter 10 and catheter tip 18 are positioned within the vascular system 92 of the patient 90 in accordance with the previous discussion. As illustrated, the catheter tip 18 is fully decompressed and conically shaped. The catheter adapter 88 is positioned on the patient 90 adjacent to the insertion site 94. The catheter adapter 88 may be secured to the patient 90 by means of a fastener, such as a steri-strip. Finally, the catheter adapter 88 is positioned and/or secured so as to permit a section of catheter tubing 12 to remain uninserted. The uninserted portion of the catheter tubing 12 provides a gentle transition from the catheter adapter to the vascular system 92 thereby preventing restricted flow through the catheter 10.

Technical Discussion

Additional objects, advantages, and novel features of this invention will become apparent to those skilled in the art upon examination of the following technical discussion. It should be appreciated that this technical discussion is not to be considered as limiting the scope of the invention, but merely as being illustrative and representative thereof.

The geometry of the conical diffuser tip reduces a nozzle recoil force of the catheter 10 thereby allowing the use of higher flow rates for infusion therapies. As previously discussed, higher flow rates are desirable for infusion therapies requiring rapid infusion of large volumes of infusate. Unlike the conical diffuser tip, conventional catheter tips taper inward thereby decreasing the inner diameter of the catheter through which an infusant exits the catheter. This tapered configuration accelerates an infusant through the tapered portion of the catheter tip. Additionally, the decreased inner diameter results in an increased back pressure or recoil force within the catheter. As previously discussed, an increased recoil force is undesirable due to the possibility of displacing the inserted catheter and/or injuring the vasculature of a patient.

Nozzle recoil force is calculated based on the principle of conservation of linear momentum. As such, the recoil force of a catheter tip may be calculated from Equation 1.

$$F_r = \frac{4Q^2\rho}{\pi}\left(\frac{1}{D_2^2} - \frac{1}{D_1^2}\right) \quad \text{Equation 1}$$

The recoil force Fr may be calculated for the catheter tip where Q is the volumetric flowrate, ρ is the density of the infusant, and the diameters D1 and D2 are first diameter and second diameter, respectively. A conventional catheter tip will comprise a second diameter D2 that is larger than the tapered first diameter D1. Therefore, according to Equation 1, a conventional catheter comprises a positive recoil force Fr dependent upon the density of the infusant. For example, for a constant volumetric flowrate Q, the recoil force Fr of the conventional catheter tip increases as the density p of the contrast media increases. Likewise, for a constant density ρ of an infusant, the recoil force Fr increases as the volumetric flowrate Q increases. An application of Equation 1 to a conventional, tapered catheter tip is explained below.

Figure 7:
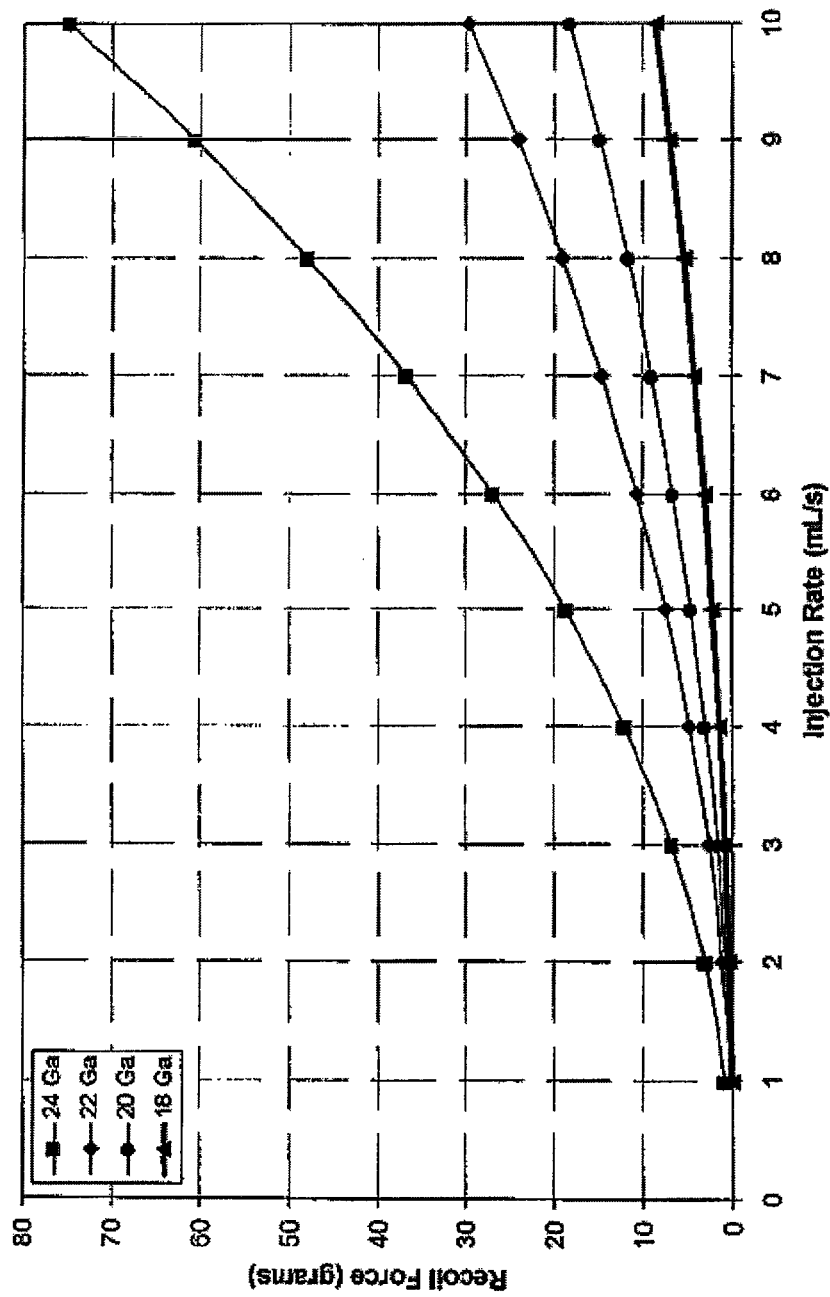
FIG. 7 is a chart demonstrating the relationship between catheter gauge, injection rate and recoil force.

A recoil force Fr was calculated for a variety of conventional catheter tips using Equation 1. Four catheters were selected including an 18, 20, 22, and 24 gauge catheters. Each catheter comprised a conventional, tapered catheter tip. A first inner diameter and a second inner diameter of the catheter tip were measured and recorded for each catheter gauge. A standard contrast media was selected with a density ρ of 1406 kg/m3. A range of volumetric flowrates Q was selected between 1 ml/second and 10 ml/second. The results are shown in FIG. 7.

As shown, the recoil force Fr for a variety of conventional, tapered catheter tips was calculated using Equation 1. According to the results, for a given injection rate (x-axis) an increase in the gauge of the catheter results in an increased recoil force Fr. Generally, a higher catheter gauge is desirable to reduce patient trauma during the placement and removal of the catheter. However, according to the results of Example 1, a higher gauge catheter, at a higher injection rate results in increased recoil force. Thus, for infusion therapies requiring high infusion rates, use of a less invasive, higher gauged conventional catheter may not be beneficial.

As demonstrated above, the recoil force of a catheter is directly proportional to the fluid velocity at the catheter tip opening. Therefore, a decrease in the fluid velocity at the catheter tip opening will result in a decreased recoil force Fr. The geometry of the conical diffuser tip provides for a decreased fluid velocity at the catheter tip. As such, the recoil force of the conical diffuser tip is decreased or eliminated. Therefore, the conical diffuser tip permits the safe use of higher gauge catheters at higher infusion rates.

Flow dynamics through a catheter is largely dependent upon the geometry of the catheter tip. Conventional catheter tips are tapered inwardly and therefore cause an infusant to accelerate while passing through the catheter tip. The flared or outwardly tapered conical diffuser tip 18, as shown in the figures, decreases the velocity of an infusant 72 while passing through the diffuser tip 18. The decreased velocity of the infusant 72 reduces or eliminates recoil force within the catheter 10. Therefore, a higher gauged catheter comprising a conical diffuser tip may be used for high infusion rate procedures without displacing the inserted catheter or damaging the patient's vasculature.

Referring again to FIG. 1, several additional geometric factors may be considered when optimizing an infusion system. An infusion system is optimized by allowing an infusant to flow, without flow separation, into an unoccluded vein. Flow separation is a disturbance whereby the flow of the infusant 72 becomes detached from the diffuser tip 18. Once detached, the flow of the infusant 72 takes the forms of eddies and vortices. The catheter tip may be configured to avoid flow separation and optimize flow of the infusant. Important geometric factors include the maximum outlet diameter 42, and the degree of divergence 44.

The maximum outlet diameter 42 is the widest point of the conical diffuser tip 18. At all infusion rates, maximal in vivo blood flow rates are significantly reduced when the maximum outlet diameter 42 of the catheter tip 18 exceeds approximately 50% of the inner diameter of the targeted vasculature. For example, where a targeted vasculature has an inner diameter of 6.0 mm, a maximum outlet diameter 42 of greater than 3.0 mm will reduce the flow efficiency of the infusion system. For this example, if the maximum outlet diameter 42 exceeds 3.0 mm, the vasculature of the patient may become occluded thereby decreasing the flow efficiency of an infusant into the patient.

Therefore, regardless of the gauge of the catheter tube 12, the maximum outlet diameter 42 of the catheter 42 must be less than, or equal to 50% of the inner diameter of a targeted vasculature. Generally, a targeted vasculature may comprise an inner diameter from about 1 mm to 1.5 cm. Commonly used veins in the forearm have an inner diameter of about 6.4 mm. Therefore, in one embodiment, a maximal outer diameter 42 will range from 0.5 mm to 0.75 cm and in another embodiment the maximum outlet diameter 42 is 3.2 mm.

The degree of divergence 44 is the angle at which the conical diffuser tip 18 is splayed. A divergence angle 44 must be chosen to provide maximum decrease of an infusant's 72 velocity through the diffuser tip 18 while minimizing flow separation. An optimal divergence angle 44 is selected from a range of about 5-20°. In one embodiment, a divergence angle 44 of less than about 14° should be selected with a preferred range of about 5-14° and an optimal divergence angle 44 of about 8°.

The geometry of the conical diffuser tip 18 is selected to minimize the infusant's velocity at the second end 26 of the catheter 10. In a preferred embodiment, the geometry of the diffuser tip 18 is selected such that the fluid velocity of an infusant 72 is slowed through the diffuser tip 18. For example, in one embodiment an infusant 72 is infused at a desired rate whereupon the diffuser tip 18 diffuses the infusant 72 such that the recoil force of the catheter 10 is eliminated. In another embodiment, the diffuser tip 18 decreased an infusant's velocity such that the inserted catheter 10 is not displaced and the vasculature of the patient is not damaged by the infusant 72. Therefore, in this embodiment the decreased velocity of the infusant 72 prevents an undesirable recoil force for the catheter 10. As such, the diffuser tip 18 prevents the infusant 72 from being accelerated into a patient's vein at an unsafe velocity during high rates of infusion.

The conical diffuser tip 18 utilizes a round cross-sectional shape. Although the present embodiment demonstrates a round cross-sectional shape, other shapes including oval, square and/or rectangular shapes may be used as needed. Generally, the geometry and shape of the catheter tubing 12 and the conical diffuser tip 18 is selected to optimize the flow of an infusant 72 through the catheter 10. Additionally, the geometry and shape of the catheter 10 and diffuser tip 18 are selected to reduce the velocity of an infusant 72 as the infusant travels through the conical diffuser tip 18.

In a preferred embodiment, the catheter 10, including the catheter tubing 12 and the diffuser tip 18, is fabricated from a polymeric material such as nylon, PVC, PVP, silicone, polyurethane and/or polyethylene. Additionally, a preferred embodiment may include a radiopaque filler, such as a chemical salt of bismuth or barium and/or an element such as platinum or tungsten.

The present invention may be embodied in other specific forms without departing from its structures, methods, or other essential characteristics as broadly described herein and claimed hereinafter. The described embodiments are to be considered in all respects only as illustrative, and not restrictive. The scope of the invention is, therefore, indicated by the appended claims, rather than by the foregoing description. All changes that come within the meaning and range of equivalency of the claims are to be embraced within their scope.

The invention claimed is:

1. An infusion device, comprising:
a catheter tube; and
a generally conical diffuser disposed on a distal end of the catheter tube, the generally conical diffuser having an outer surface that generally increases in diameter from a proximal end of the generally conical diffuser to a distal end of the generally conical diffuser, the generally conical diffuser tip also having an inner surface that generally increases in diameter from the proximal end to the distal end, the diameter of the inner surface increasing at a higher rate than the diameter of the outer surface such that the width of a wall of the generally conical diffuser tip is greater at the proximal end than at the distal end.

2. The infusion device of claim 1, wherein the diameter of the inner surface at the proximal end is approximately equal to an inner diameter of the catheter tube.

3. The infusion device of claim 1, wherein the generally conical diffuser tip comprises a different material than the catheter tube.

4. The infusion device of claim 1, wherein the generally conical diffuser tip is mechanically compressed and slidably housed within an introducer needle.

5. The infusion device of claim 4, wherein the introducer needle is splittable.

6. The infusion device of claim 1, wherein the generally conical diffuser tip is dehydrated and thereby compressed and slidably housed within an introducer needle.

7. The device of claim 1, further comprising a rapid infusion pump in fluid communication with the catheter tube, and wherein the catheter tube is a peripheral venous catheter.

8. A method for manufacturing an infusion device, the method comprising:
providing a catheter tube;
joining a generally conical diffuser tip to a distal end of the catheter tube, the generally conical diffuser tip including an outer surface that generally increases in diameter from a proximal end of the generally conical diffuser to a distal end of the generally conical diffuser, the generally conical diffuser tip also including an inner surface that generally increases in diameter from the proximal end to the distal end, the diameter of the inner surface increasing at a higher rate than the diameter of the outer surface such that the width of a wall of the generally conical diffuser tip is greater at the proximal end than at the distal end.

9. The method of claim 8, wherein the generally conical diffuser tip comprises a different material than the catheter tube.

10. The method of claim 9, wherein the generally conical diffuser tip comprises a material that swells when exposed to blood.

11. The method of claim 8, further comprising providing a rapid infusion pump in fluid communication with the catheter tube, and wherein the catheter tube is a peripheral venous catheter.

12. An infusion apparatus comprising: a catheter; and a generally conical diffuser tip attached to an end of the catheter, wherein an outer surface of the generally conical diffuser tip splays outwardly from a first diameter at a proximal end of the generally conical diffuser tip to a second diameter at a distal end of the generally conical diffuser tip, the distal end forming an outlet end, wherein the thickness of a wall of the generally conical diffuser tip is greater at the proximal end than at the distal end; and the generally conical diffuser tip also having an inner surface that generally increases in diameter from the proximal end to the distal end, the diameter of the inner surface increasing at a higher rate than the diameter of the outer surface such that the width of a wall of the generally conical diffuser tip is greater at the proximal end than at the distal end.

13. The infusion apparatus of claim 12, wherein the generally conical diffuser tip comprises a different material than the catheter.

14. The infusion apparatus of claim 12, wherein the generally conical diffuser tip is mechanically compressed and slidably housed within a splittable introducer needle.

15. The infusion apparatus of claim 12, wherein the generally conical diffuser tip comprises a material that swells when exposed to blood.

16. The apparatus of claim 12, further comprising a rapid infusion pump in fluid communication with the catheter, and wherein the catheter is a peripheral venous catheter.

17. The infusion apparatus of claim 12, wherein the generally conical diffuser tip is joined to the catheter via one of induction, electrofusion, laser welding, mechanical bonding, or chemical bonding.

18. The infusion apparatus of claim 12, wherein a geometry of the generally conical diffuser tip reduces a nozzle recoil force of the catheter.

19. The infusion apparatus of claim 12, further comprising an infusant located within the catheter, wherein a velocity of the infusant is decreased when the infusant is moved from within the catheter to within the generally conical diffuser tip.

20. The infusion apparatus of claim 12, further comprising:
a splittable introducer needle within which the catheter and generally conical diffuser tip are housed, the splittable introducer needle having score marks along which the splittable introducer needle splits into a first half and a second half, the splittable introducer needle also having a first and a second gripping handle connected to the first and second halves respectively.

* * * * *